United States Patent [19]

McRae

[11] Patent Number: Plant 6,503

[45] Date of Patent: Jan. 3, 1989

[54] HYBRID ORIENTAL LILY NAMED MARKOVA

[75] Inventor: Edward A. McRae, Boring, Oreg.

[73] Assignee: Melridge, Inc., Gresham, Oreg.

[21] Appl. No.: 38,761

[22] Filed: Apr. 15, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new variety of hybrid Oriental lily plant bearing large, upright to semi-upright flowers particularly characterized by their unspotted, pure white coloration; the large size and substance of the flowers and their orientation being a combination that is completely new in the Oriental hybrid divisions of lilies suited to forcing and to mass commercial cultivation. This plant is highly resistant to disease, shows tolerance of virus, is an excellent garden plant, and has bulbs which may be precooled and forced for cut flower production.

1 Drawing Sheet

BACKGROUND OF THE NEW PLANT

This new variety of lily plant originated as a seedling which first flowered at Sandy, Oreg., in 1970 among a group of seedlings planted by me with the object of producing large flowered, upright and semi-upright Oriental hybrids in shades of soft pink and white, suited to forcing into flower out-of-season, a variety heretofore unknown in the lily breeding art. The seedlings planted by me and among which the present variety appeared came from a mother plant which was a selection from the 'Pink Glory' strain pollinated from a selected clone of the species *Lilium nobilissimum,* this cross being accomplished by maintaining the mother plant in extremely high greenhouse temperatures for at least one week after pollination.

This particular seedling was selected for propagation because its flowers were characterized by an upright to semi-upright orientation, extremely large size, broad tepalled, "bowl-shaped" form, with unusually thick substance, and a distinctive unspotted, pure white coloration, a combination unique among Oriental hybrid lilies. This seedling was asexually reproduced by me and under my direction at Sandy, Oreg., and since the product conformed so well with my objectives, propagation was continued under my direction through several successive generations, at Sandy, Oreg., by natural propagation from bulblets, by bulb scale propagation, and by tissue culturing from bulb scale explants, all of which demonstrated that the novel and distinctive characteristics of the original seedling hold true under asexual propagation from generation to generation and appear to be firmly fixed.

This new plant possesses strong, stout stems, with exceptionally broad leaves, and the clone is found to possess to a high degree the desirable characteristics of hybrid vigor, great hardiness, and disease resistance; with excellence of form, color, and habit.

This new variety has also been found to be well suited to forcing out-of-season when the bulbs are dug at the appropriate time and properly precooled. For example, late October-dug bulbs, properly precooled and potted in January, will flower under glass in western Oregon in an average of one hundred to one hundred and fifteen days with no supplementary lighting and at moderate greenhouse temperatures.

DESCRIPTION OF THE DRAWING

This new variety of lily plant is illustrated by the accompanying photographic drawing, which shows a fully opened bloom in full color and illustrates the flower form and tepal arrangement and, in particular, the novel and distinctive flower size, form and upright orientation, as well as its unspotted, pure white coloration.

DESCRIPTION OF THE NEW VARIETY

The following is a detailed description of my new variety of hybrid Oriental lily, with nomenclature according to The International Lily Register of The Royal Horticultural Society at London, Second Edition, 1969, and with color designations according to The R.H.S. Colour Chart published by The Royal Horticultural Society in 1966.

THE PLANT

Origin: Seedling.

Parentage:

*Seed parent.*—A selected clone from the 'Pink Glory' strain (unpatented).

*Pollen parent.*—A selected clone of *Lilium nobilissimum* (unpatented).

Classification:

*Horticultural.*—Division VII-B, Bowl-shaped Oriental Hybrid Lily according to The Horticultural Classification of Lilies by The Royal Horticultural Society of London, England.

*Commercial.*—Hybrid Lilium Clone.

Form: A single stem, erect and stately.

Height: About 70 to 125 cm., according to age, from bulbs of about 14 to 18 cm. in circumference, provided that their light levels are adequate. Low light levels may cause "stretching".

Growth: Upright and vigorous.

Foliage:

*Quantity.*—Abundant.

*Leaf size.*—Unusually broad, about 7 to 8 cm. wide and about 12 to 15 cm. long.

*Leaf shape.*—Lanceolate and acuminate.

*Texture.*—Leathery.

*Aspect.*—Glossy.

*Color.*—Medium green, somewhat lighter on the lower side.

Bulbs:

*Size.*—Varying and ranging up to 25 cm. in circumference as commercially used.

*Color.*—White, with flushes of soft pink or soft yellow.

THE BUD

Form: Long ovoid and obtuse.

Size: About 9 to 12 cm. long and about 10 to 12 cm. in circumference just prior to opening.

Opening date: The bud opens slowly, taking about one hour in response to morning light.

Color: Soft pink with deeper midribs overlaying soft green.

Peduncle:

*Length.*—About 4 to 6 cm., in average, but may elongate somewhat if light levels are too low or if bulbs have been improperly stored prior to forcing.

*Color.*—Medium green with very light plum overlay.

THE FLOWER

Blooming habit: Once annually and profusely in midseason.

Size: Large; averaging about 18 to 23 cm. in diameter. The tips reflex during the second day to provide a spread of about 15 to 18 cm. in diameter.

Borne: As a single raceme having about three to six flowers from a bulb of about 14 to 18 cm. in circumference.

Shape: Opening to a broad bowl shape by the second day with the bowl having a depth of about 10 cm.

Tepalage:

*Number.*—Typical of the genus Lilium with six imbricated tepals in hexagonal arrangement.

*Size.*—The outer tepals are 3 to 3.5 cm. wide and the inner tepals are 5 to 5.5 cm. wide.

*Color.*—Pure white. Under unusually cool, bright conditions, soft flushes of pale pink may occasionally appear on the tepals. The nectary furrows are apple green.

Spotting: The flowers are completely unspotted.

Appearance: The flower is shiny.

Fragrance: Heavy, but pleasing.

Lasting quality: The tepals stay on the stems for about three weeks and, in general, the flowers are long lasting both on the plant and as cut flowers.

Pedicel:

*Length.*—About 8 to 12 cm., in average.

*Form.*—Sturdy and ascending up to about 45 degrees from the horizontal.

*Color.*—Medium green with light plum overlay.

Disease resistance: The flower and plant are resistant to disease; in particular, they are resistant to Fusarium bulb rot and Botrytis blight, as observed in western Oregon.

REPRODUCTIVE ORGANS

Stamens:

*Number.*—Six.

*Arrangement.*—Typical of the genus Lilium.

*Anthers (dehisced) and pollen.*—Color: Greyed red, 179A.

*Filaments.*—Length: About 8 to 10 cm. Color: Soft green to white.

Pistil:

*Number.*—One.

*Length.*—About 8 to 10 cm.

*Stigma.* 13 Size: Large. Color: Soft greenish white to very light pink.

Characteristics of Ovary: The ovary characteristics are the same as those of the genus Lilium.

THE FRUIT

Fertility: The fruit is fertile.

Shape: Ovoid.

Color at maturity: Soft brown, sometimes overlaid with soft plum.

The new variety of hybrid Oriental lily most nearly resembles *Lilium nobilissimum* but is taller, and with stronger stems. Also, the buds of the new variety and its flowers have a soft pink reverse side unlike *Lilium nobilissimum.* The flowers of the new variety are not as completely upfacing as those of *Lilium nobilissimum* and its flower form is larger, conspicuously broader-tepalled, less trumpet-formed, and more bowl-shaped.

I claim:

1. The new and distinct variety of hybrid Oriental lily plant and parts thereof, substantially as herein shown and described, and particularly characterized by its semi-upright to upright flowers of pure white, unspotted coloration; by the excellence of its flower form, and by its versatility as a garden plant and as a cut flower producer from precooled bulbs forced under glass out-of-season.

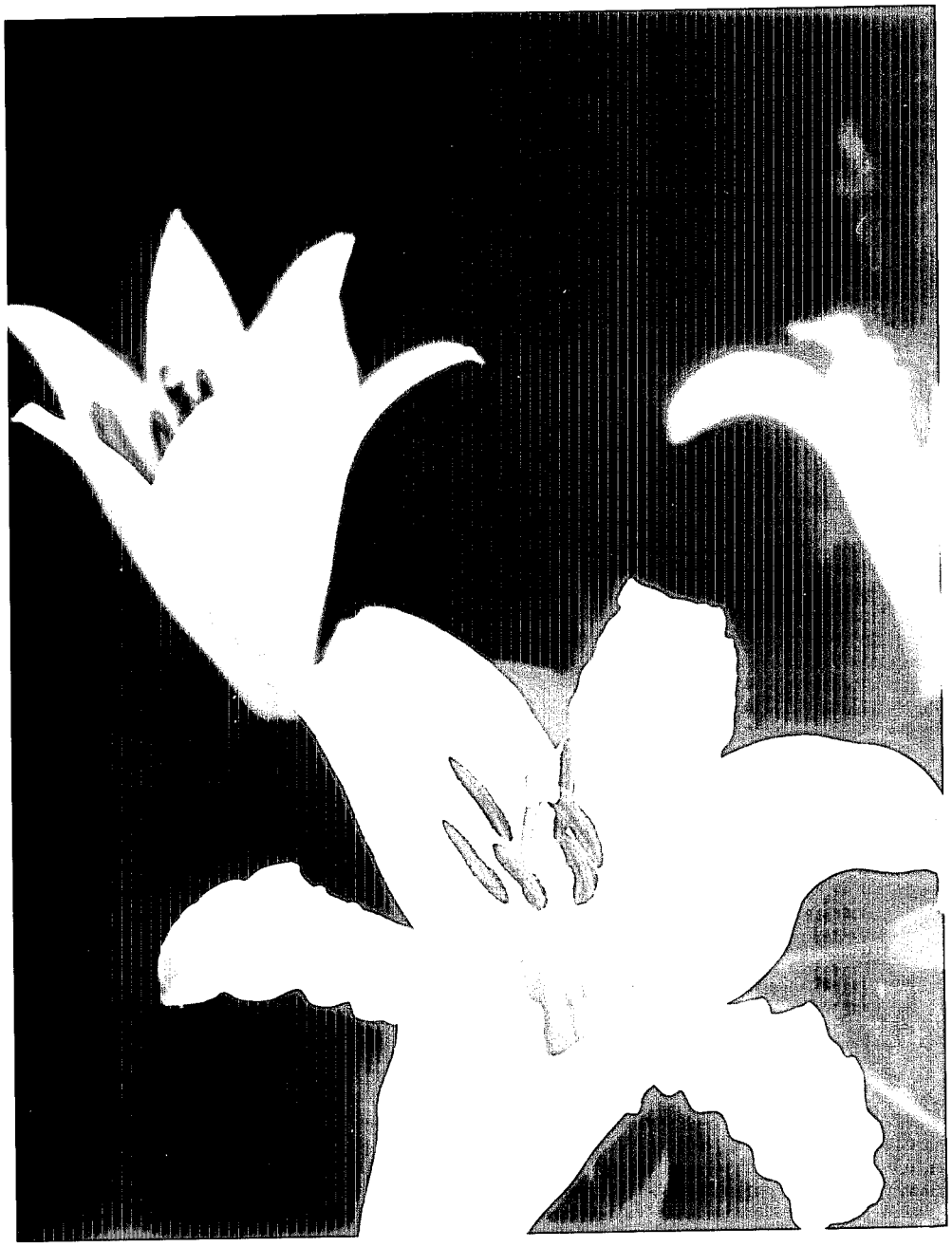

* * * * *